United States Patent [19]

Hofmeister et al.

[11] Patent Number: 4,550,100

[45] Date of Patent: Oct. 29, 1985

[54] PROCESS FOR THE PREPARATION OF 17α-BROMOETHYNYL- AND 17α-IODOETHYNYL-17β-HYDROXY STEROIDS AND NOVEL PRODUCTS THEREOF

[75] Inventors: Helmut Hofmeister; Paul E. Schulze; Klaus Annen; Henry Laurent; Rudolf Wiechert, all of Berlin, Fed. Rep. of Germany

[73] Assignee: Schering Aktiengesellschaft, Berlin and Bergkamen, Fed. Rep. of Germany

[21] Appl. No.: 552,537

[22] Filed: Nov. 16, 1983

[30] Foreign Application Priority Data

Nov. 16, 1982 [DE] Fed. Rep. of Germany ....... 3242892

[51] Int. Cl.$^4$ .................. C07J 1/00; A61K 31/56
[52] U.S. Cl. ................................ 514/179; 514/182
[58] Field of Search .................. 260/397.5, 397.45

[56] References Cited

U.S. PATENT DOCUMENTS 3,121,079 2/1964 Oberster et al. ............... 260/397.4
3,959,322 5/1976 Hughes et al. ................. 260/397.4

FOREIGN PATENT DOCUMENTS 1132206 10/1968 United Kingdom ............ 260/397.4

OTHER PUBLICATIONS

Burgess et al., Tetrahedron 23; (1967), pp. 4111-4116.

Mazaitis, The Journal of Nuclear Medicine (1980) 21; pp. 142-146.
Salomon et al., Helv. Chim. Acta 30:1616 (1947).

*Primary Examiner*—Elbert L. Roberts
*Attorney, Agent, or Firm*—Millen & White

[57] ABSTRACT

A process for preparing bromine- or iodine-unlabeled or radioactively labeled 17α-bromoethynyl- and 17α-iodoethynyl-17β-hydroxy steroids of the androstane and estrane series of the partial formula

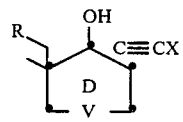

wherein is a single bond or a double bond,
V is a carbon-carbon bond or a methylene group,
R is hydrogen or methyl, and
X is bromine or iodine, from corresponding 17α-ethynyl-17β-hydroxy steroids, comprises treating the starting steroid in an inert solvent with a brominating agent or an iodinating agent in the presence of a silver salt.

The process enables production of old and new compounds having value as pharmacologically active compounds and also as diagnostic agents when the iodine or bromine is radioactive.

26 Claims, No Drawings

PROCESS FOR THE PREPARATION OF 17α-BROMOETHYNYL- AND 17α-IODOETHYNYL-17β-HYDROXY STEROIDS AND NOVEL PRODUCTS THEREOF

BACKGROUND OF THE INVENTION

17α-Haloethynyl-17β-hydroxy steroids of the androstane and estrane series can be conventionally prepared by blocking 3- and 17β-positioned oxygen functions of a 4(5)-unsaturated steroid, reacting the thus-obtained compound under reflux with potassium tertbutylate and a halogenating agent, such as N-bromosuccinimide in a tertiary alcohol, and then splitting off the blocking groups (DAS 1,242,607).

Another method uses trifluorobromomethane as the brominating agent; this compound is made to react in liquid ammonia with the lithium salt of the 17α-ethynyl steroid. Here, too, the oxygen functions on the C-3 atom and the 17β-hydroxy group must be blocked [Tetrahedron 23:4111 (1967)].

Known 17α-iodoethynyl steroids thus far are only 17α-iodoethynyl-1,3,5(10)-estratriene-3,17β-diol and its 11β-methoxy derivative, obtained from 3-benzoyloxy-17α-ethynyl-1,3,5(10)-estratrien-17β-ol and, respectively, from its 11β-methoxy derivative by reaction with morpholine and iodine or with chloramine-T and sodium iodide and subsequent saponification of the 3-benzoyloxy group [J. Nucl. Med. 21:142 (1980)].

SUMMARY OF THE INVENTION

It is an object of the present invention to provide a process for the preparation of 17α-bromoethynyl- or 17α-iodoethynyl-17β-hydroxy steroids from the corresponding 17α-ethynylcarbinols, making it possible to halogenate the 17α-ethynyl group without blockage of the 17β-hydroxy group or any present 3-keto group.

Upon further study of the specification and appended claims, further objects and advantages of this invention will become apparent to those skilled in the art.

These objects has been attained by this invention by a process comprising adding a catalytic amount of a silver salt to the reaction mixture comprising the brominating or iodinating agent and the starting steroid. The reaction can be conducted in a protonic or aprotic solvent or in solvent mixtures.

Hence, this invention relates to a process for the preparation of bromine- and iodine-unlabeled and radioactively labeled 17α-bromoethynyl- and 17α-iodoethynyl-17β-hydroxy steroids of the androstane and estrane series, e.g., of the partial formula

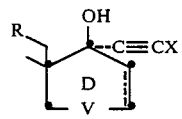

wherein
 is a single bond or a double bond,
V is a carbon-carbon bond or a methylene group,
R is a hydrogen or methyl, and
X is bromine or iodine,
from corresponding 17α-ethynyl-17β-hydroxy steroids,
comprising treating the starting steroid in an inert solvent with a brominating agent or an iodinating agent in the presence of a silver salt.

DETAILED DISCUSSION

A key feature of this invention resides in the use of a silver salt as the catalyst. It is utilized in an amount of 1/1000 to 1 molar equivalent, preferably 1/100 to 1/10 molar equivalent, based on the amount of starting steroid. Suitable silver salts include, for example, silver nitrate, silver perchlorate, silver acetate, silver trifluoroacetate, silver fluoride, silver sulfate and the like. In essence, any silver salt can be utilized as long as the anion is reaction compatible. In other words, the nature of the anion is not critical. Of course, it is also required that the silver salt be sufficiently soluble or dispersible in the solvent to provide the amount of silver cations mentioned above.

Suitable brominating and iodinating agents are agents releasing bromine or iodine anions. These are generally conventional. Suitable for bromination are N-bromosuccinimide, N-bromoacetamide, N-bromophthalimide, N-bromo-p-toluenesulfamide, N-bromo-p-toluenesulfimide, N-bromocaprolactam, sodium hypobromide, or 1,3-dibromo-5,5-dimethylhydantoin. Especially suitable is N-bromosuccinimide. N-Iodosuccinimide is preferred as the iodinating agent.

The halogenating agent is generally utilized in an equimolar amount based on the amount of starting steroid, but an excess amount is also possible.

Suitable solvents include all those which are inert with respect to the halogenating agent and the silver salt. Especially suitable are solvents such as ketones, e.g., acetone, cyclohexanone, methyl ethyl ketone, and methyl isobutyl ketone; cyclic ethers, e.g., tetrahydrofuran and dioxane; aliphatic polyethers, such as ethylene glycol dimethyl ether and diethylene glycol dimethyl ether; aromatic hydrocarbons, such as benzene or toluene; aliphatic alcohols, such as methanol, ethanol, and propanol; and solvents such as dimethylformamide, dimethylacetamide, hexamethylphosphoric triamide, or N-methylpyrrolidone, as well as mixtures of water-miscible solvents and water. The solvents can be utilized individually, if they form a solution or suspension with the starting steroid, or also in the form of a mixture with one another. Typically, the solvent constitutes 70–99 wt% of the reaction mixture.

The 17α-ethynyl-17β-hydroxy steroids employable as starting materials can be conventionally substituted as desired. These steroids can belong to the androstane or estrane series. In the steroid molecule, in the A-, B-, C-, and D-rings, isolated double bonds can be present in the 4-, 5-, 5(10)-, 6-, 8-, 9(11)-, 11-, and/or 15-positions, and aromatic double bonds can be present in the 1,3,5(10)-position. $C_{1-4}$-alkyl or $C_{2-4}$-alkenyl groups, such as methyl, ethyl, or methylene can be present, for example, in the 1-, 6-, or 11-position. $C_{1-4}$-alkoxy groups, such as methoxy or ethoxy, can be present, for example, in the 3-position as can keto or hydroxy groups. Structures of typical androstanes and estranes which can be used include those disclosed in U.S. Pat. Nos. 4,119,626; 3,959,322; 3,927,046 and 4,081,537 whose disclosures are incorporated by reference herein.

The reaction of this invention can be carried out in a temperature range from 0° to 50° C. and is preferably conducted at room temperature. The reaction is generally completed, depending on the solvent employed, within 10 minutes up to 20 hours. The completion can be conventionally determined, for example, by thin-layer chromatography.

After the reaction is finished, the reaction mixture is worked up as usual, for example by precipitation, washing, extraction, recrystallization, and/or column chromatography.

The course of the reaction according to this invention was unexpected and therefore surprising, inasmuch as a reaction at the 17α-ethynylcarbinol system with hypobromous acid, produced from N-bromosuccinimide or N-bromoacetamide with tert-butanol/water, takes place only if the 17β-hydroxy group is esterified. In contrast to the method of this invention catalyzed with silver salt, the product in this prior art process is not a 17α-bromoethynyl steroid, but rather a 21-dibromoketone [Salomon et al., Helv. Chim. Acta 30:1616 (1947)].

Furthermore, it has also been found that if N-chlorosuccinimide and a catalytic amount of a silver salt is added to a suspension of 17α-ethynyl-17β-hydroxy-4-androsten-3-one in acetone/water, surprisingly, there is no reaction to the corresponding 17α-chloroethynyl compound. Therefore, it was definitely surprising that, under the same reaction conditions, with N-bromo- or N-iodosuccinimide, respectively, the 17α-bromoethynyl- or 17α-iodoethynyl-4-androsten-3-one, respectively, was obtained in a high yield.

The process of this invention for the production of 17α-bromo- and 17α-iodoethynyl steroids from the corresponding 17α-ethynyl-17β-hydroxy compounds has the further advantages as compared with the known methods that it is a one-step process, and that the yields of 17α-haloethynyl steroids are, in the majority of cases, very high, e.g., 80–92 mole%.

17α-bromo- and 17α-iodoethynyl steroids can be used as starting compounds for the preparation of the corresponding, radioactively labeled 17α-haloethynyl compounds. Thus, it is possible in accordance with a novel method of radiochemistry to produce 17α-[*I]-iodoethynyl compounds from 17α-iodo- or 17α-bromoethynyl steroids by exchange reaction over 0.5–5 hours with radioactive sodium [*I]-iodide in acetone at reflux, in an inert atmosphere. Analogously, the corresponding 17α-[*Br]-bromoethynyl compounds are formed from 17α-iodo- and 17α-bromoethynyl steroids by exchange reaction over 0.5–5 hours with radioactive sodium [*Br]-bromide with the addition of copper sulfate (0.05–5 moles per mole of steroid), preferably in acetone, at reflux, in an inert atmosphere. These 17α-[*Br]-bromoethynyl compounds can also be produced according to a known reaction [J. Label Comp. and Radiopharmaceuticals 18:1033 (1980)] from iodoethynyl steroids by reaction with sodium [*Br]-bromide and chloramine T. The radioisotope labeling with bromine and iodine isotopes, respectively, can also be achieved by using radioactive bromo- or iodosuccinimide, and reacting 17α-ethynyl steroids with the radioactive halosuccinimide with the addition of catalytic amounts of a silver salt, in acetone/water, for example, in the process of this invention. In the novel exchange reactions, $10^{-4}$–$10^2$ moles of radioactive halo salt are used per mole of steroid.

Labeled 17α-haloethynyl steroids are of interest in medical diagnostics. Thus, 17α-[$^{125}$I]-iodoethynylestradiol [J. Nucl. Med. 21:142 (1980)] or 17α-[$^{77}$Br]-bromoethynylestradiol [J. Label Comp. and Radiopharmaceuticals 18:1033 (1980) is utilized for locating breast tumors. The novel 17α-bromoethynyl- and 17α-iodoethynyl-17β-hydroxy steroids of Formulae I and II below can be utilized in diagnostic agents in fully analogous fashion.

Novel compounds preparable by this invention include 17α-bromoethynyl- or 17α-iodoethynyl-17β-hydroxy steroids of Formulae I and II

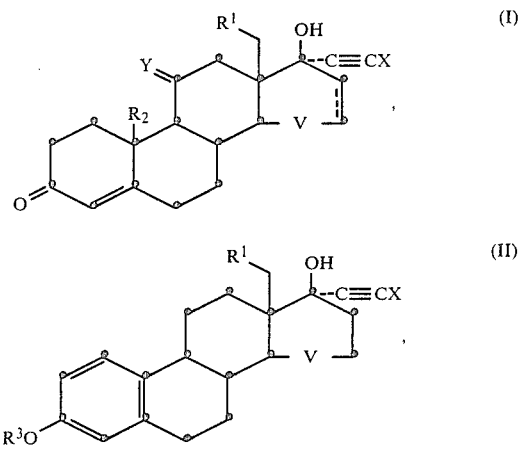

wherein

─ ─ ─ ─, X and V, are as defined above,

Y is two hydrogen atoms or a methylene group, $R^1$ and $R^2$ each individually is hydrogen or methyl, and $R^3$ is $C_{1-4}$-alkyl or, when X is bromine, also is hydrogen.

Particularly useful are 17α-bromoethynyl- or 17α-iodoethynyl-17β-hydroxy steroids of Formulae I and II wherein X is a radioactive bromine or iodine isotope.

All of the compounds producible by the process of this invention are conventional or novel materials having an activity profile which is essentially the same as that of the corresponding compounds which are not substituted by halogen. Thus, the compounds of Formula I have progestational activity, just as, for example, does levonorgestrel. The compounds of Formula II have estrogenic activity, just as ethynylestradiol does, for example. As mentioned above, these compounds can also serve as diagnostic agents in medicine, just as, for example, 17α-[*Br]-bromo- or 17α-[*I]-iodoethynylestradiol [J. Nucl. Med. 21:142 (1980)].

All compounds producible by the process of this invention are thus useful at least as radioactive diagnostic agents or as non-radioactive I- or Br-containing steroids which can be used as intermediates for the preparation of the corresponding radioactive I- or Br-compounds, using methods disclosed herein, the latter being useful diagnostically.

The compounds can be used for the mentioned purposes in mammals including humans. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrum, elixir or the like can be used wherein a sweetened vehicle is employed. Sustained release compositions can be formulated including those wherein the active compound is protected with differentially degradable coatings, e.g., by microencapsulation, multiple coatings, etc.

Dosages for a given host for a given indication can be determined, e.g., by customary comparison of the activities of the subject compound and of a known agent by means of an appropriate, conventional pharmacological protocol.

Dosages and regimens of administration are fully analogous to the conventional analogous agents mentioned above for each of the mentioned uses. Typically, the unit dosage for progestational or estrogenic use is 0.01–0.5 mg and the daily dosage for human beings, respectively, is 0.05–0.5 mg and 0.01–10 mg. Total dosages are conventionally determined to provide adequate visualization of hot spots.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A suspension of 2.0 g of 17α-ethynyl-17β-hydroxy-18-methyl-4-estren-3-one in 40 ml of acetone and 6 ml of water is combined at room temperature with 1.4 g of N-bromosuccinimide and 60 mg of silver nitrate. After 30 minutes, the reaction mixture is introduced into ice/water. The thus-precipitated product is suctioned off, washed with water, dissolved with ethyl acetate, and dried over sodium sulfate. Recrystallization of the crude product from acetone/hexane yields 2.0 g of 17α-bromoethynyl-17β-hydroxy-18-methyl-4-estren-3-one. Melting point: 206.4° C.—yield 80% of theory.

EXAMPLE 2

A room temperature, 1.5 g of 1,3 dibromo-5,5-dimethylhydantoin and 50 mg of silver nitrate are added to 1.5 g of 17α-ethynyl-3-methoxy-D-homo-1,3,5(10)-estratrien-17aβ-ol in 30 ml of acetone and 4 ml of water. After 30 minutes, the reaction mixture is stirred into ice/water. The thus-precipitated product is suctioned off, washed with water, and dissolved in ethyl acetate. Chromatography of the crude product on silica gel with acetone/hexane yields 1.3 g of 17aα-bromoethynyl-3-methoxy-D-homo-1,3,5(10)-estratrien-17aβ-ol, isolated in the form of a foam. Yield 70% of theory.

EXAMPLE 3

As described in Example 1, but using toluene/acetone (85:15) as the solvent, 17α-ethynyl-17β-hydroxy-18-methyl-4-estren-3-one is reacted at room temperature (reaction time 5 hours) and processed into 17α-bromoethynyl-17β-hydroxy-18-methyl-4-estren-3-one. Melting point: 203.5° C.—yield 64% of theory.

EXAMPLE 4

As described in Example 1, but with the use of 1,3-dibromo-5,5-dimethylhydantoin as the brominating agent, 17α-ethynyl-17β-hydroxy-18-methyl-4-estren-3-one is reacted at room temperature (reaction time one hour) and worked up into 17α-bromoethynyl-17β-hydroxy-18-methyl-4-estren-3-one. Melting point: 204.3° C.—yield 72% of theory.

EXAMPLE 5

As described in Example 1, but utilizing ethanol as the solvent, 17α-ethynyl-17β-hydroxy-4-estren-3-one is reacted at room temperature (reaction time 30 minutes) and processed into 17α-bromoethynyl-17β-hydroxy-4-estren-3-one. Melting point: 182.5° C.—yield 64% of theory.

EXAMPLE 6

As disclosed in Example 1, but with the use of 1-methyl-2-pyrrolidone as the solvent and silver trifluoroacetate as the catalyst, 17α-ethynyl-17β-hydroxy-4-estren-3-one is reacted at room temperature (reaction time 15 minutes) and processed into 17α-bromoethynyl-17β-hydroxy-4-estren-3-one. Melting point: 184.6° C.—yield 80% of theory.

EXAMPLE 7

As described in Example 1, but utilizing acetone as the solvent and silver acetate as the catalyst, 17α-ethynyl-17β-hydroxy-4-androsten-3-one is reacted at room temperature (reaction time 45 minutes) and worked up to 17α-bromoethynyl-17β-hydroxy-4-androsten-3-one. Melting point: 183.7° C.—yield 88% of theory.

EXAMPLE 8

As disclosed in Example 1, but with the use of N-bromoacetamide as the brominating agent, 17α-ethynyl-17β-hydroxy-4-androsten-3-one is reacted at 30° C. (reaction time 20 hours) and processed into 17α-bromoethynyl-17β-hydroxy-4-androsten-3-one. Melting point: 181.5° C.—yield 45% of theory.

EXAMPLE 9

As set forth in Example 1, but using tetrahydrofuran as the solvent, 17α-ethynyl-17β-hydroxy-18-methyl-11-methylene-4-estren-3-one is reacted at 15° C. (reaction time 30 minutes) and worked up into 17α-bromoethynyl-17β-hydroxy-18-methyl-11-methylene-4-estren-3-one. Melting point: 203.8° C.—yield 92% of theory.

EXAMPLE 10

As described in Example 1, but employing 1,2-dimethoxyethane as the solvent, 17α-ethynyl-18-methyl-11-methylene-4-estren-17β-ol is reacted at 10° C. and worked up into 17α-bromoethynyl-18-methyl-11-methylene-4-estren-17β-ol. Melting point: 168.8° C.—yield 51% of theory.

EXAMPLE 11

As described in Example 1, but using silver acetate as the catalyst, 17α-ethynyl-17β-hydroxy-18-methyl-4,15-estradien-3-one is reacted at room temperature (reaction time 20 minutes) and processed into 17α-bromoethynyl-17β-hydroxy-18-methyl-4,15-estradien-3-one. Decomposition point: 110° C.—yield 50% of theory.

EXAMPLE 12

As set forth in Example 1, but using 2-butanone as the solvent, 17aα-ethynyl-3-methoxy-1,3,5(10)-estratrien-17β-ol is reacted at room temperature (reaction period one hour) and worked up into 17aα-bromoethynyl-3-methoxy-1,3,5(10) -estratrien-17β-ol. Melting point: 172.6° C.—yield 84% of theory.

EXAMPLE 13

As disclosed in Example 1, but employing dimethylformamide/water (85:15) as the solvent, 17α-ethynyl-1,3,5(10) -estratriene-3,17β-diol is reacted at room temperature (reaction period 4 hours) and processed into 17α-bromoethynyl-1,3,5(10)-estratriene-3,17β-diol. Melting point: 169.6° C.—yield 46% of theory.

EXAMPLE 14

At room temperature, 900 mg of N-iodosuccinimide and 50 mg of silver nitrate are added to a solution of 1.0 g of 17α-ethynyl-17β-hydroxy-4-estren-3-one in 20 ml of acetone and 3 ml of water. After 30 minutes, the reaction mixture is stirred into ice/water. The thus-precipitated product is suctioned off, washed with water, dissolved in ethyl acetate, and dried over sodium sulfate. After recrystallization from acetone/hexane, 1.1 g of 17β-hydroxy-17α-iodoethynyl-4-estren-3-one is obtained. Decomposition point: 168° C.—yield 77% of theory.

EXAMPLE 15

At room temperature, 610 mg of N-iodosuccinimide and 50 mg of silver nitrate are added to 800 mg of 17aα-ethynyl-3-methoxy-D-homo-1,3,5(10)-estratrien-17aα-ol in 20 ml of acetone and 3 ml of water. After 20 minutes, the reaction mixture is stirred into ice/water. The thus-precipitated product is suctioned off, washed with water, and dissolved in ethyl acetate. Chromatography of the crude product on silica gel with acetone/hexane yields 650 mg of 17aα-iodoethynyl-3-methoxy-D-homo-1,3,5(10)-estratrien-17aα-ol as a foam. Yield 59% of theory.

EXAMPLE 16

As described in Example 14, but using acetone as the solvent and silver trifluoroacetate as the catalyst, 17α-ethynyl-17β-hydroxy-4-androsten-3-one is reacted at 15° C. (reaction time 30 minutes) and worked up into 17β-hydroxy-17α-iodoethynyl-4-androsten-3-one. Decomposition point: 164° C.—yield 79% of theory.

EXAMPLE 17

As described in Example 14, but with the use of tetrahydrofuran as the solvent, 17α-ethynyl-17β-hydroxy-18-methyl-4-estren-3-one is reacted at 10° C. (reaction time 45 minutes) and worked up into 17β-hydroxy-17α-iodoethynyl-18-methyl-4-estren-3-one. Decomposition point: 157° C.—yield 86% of theory.

EXAMPLE 18

As disclosed in Example 14, but using 1,2-dimethoxyethane as the solvent and silver acetate as the catalyst, 17α-ethynyl-17β-hydroxy-18-methyl-11-methylene-4-estren-3-one is reacted at 15° C. (reaction period 30 minutes) and processed into 17β-hydroxy-17α-iodoethynyl-18-methyl-11-methylene-4-estren-3-one. Decomposition point: 180° C.—yield 56% of theory.

EXAMPLE 19

As described in Example 14, but employing dioxane as the solvent, 17α-ethynyl-3-methoxy-1,3,5(10)-estratrien-17β-ol is reacted at 20° C. (reaction time 1¾ hours) and worked up into 17α-iodoethynyl-3-methoxy-1,3,5(10)-estratrien-17β-ol. Melting point: 145° C.—yield 86% of theory.

EXAMPLE 20

As disclosed in Example 14, 17α-ethynyl-17β-hydroxy-18-methyl-4,15-estradien-3-one is reacted at room temperature (reaction period 20 minutes) and worked up into 17β-hydroxy-17α-iodoethynyl-18-methyl-4,15-estradien-3-one. Decomposition point: 167° C.—yield 64% of theory.

EXAMPLE 21

9 mg (0.14 millimole) of N-iodosuccinimide is suspended with 1 ml of acetone and heated under reflux in the presence of 37 MBq (1 mCi) of Na$^{125}$I (carrier-free). (In the TLC system, the progress and termination of exchange between radioactive iodide in the solution and the inactive iodine in the molecule are checked out.)

After cooling, 0.15 ml of water and 10 mg (32 μmol) of 17α-ethynyl-17β-hydroxy-18-methyl-4-estren-3-one are added to the reaction mixture, and thereafter 0.6 mg (100 μmol) of silver nitrate is added as well.

The progression of the reaction is observed with a TLC system of ether/chloroform (8:2), and the reaction is interrupted after about one hour under agitation at room temperature.

The solution is diluted with water and extracted with ethyl acetate. The ethyl acetate phase is washed neutral with water and concentrated. The crude compound is purified by chromatography over a low-pressure column. The eluent employed is hexane/ethyl acetate (ethyl acetate 0–30%). The product is 4.07 MBq (110 μCi) of 17β-hydroxy-17α-[$^{125}$I]-iodoethynyl-18-methyl-4-estren-3-one having a specific activity of about 260 MBq/mmol (7 mCi/mmol).

EXAMPLE 22

5 μg (0.011 μmol) of 17β-hydroxy-17α-iodoethynyl-18-methyl-4-estren-3 one is dissolved in 0.25 ml of acetone (p.a.) and heated under reflux for one hour under a protective gas with 370 MBq of sodium [$^{131}$I]-iodide of highest specific activity. After cooling to ice bath temperature, 0.25 ml of methanol, 0.1 ml of water, and 1 μg of sodium iodide are added thereto. To remove the ions, the solution is passed through a mixed bed ion exchanger, thus obtaining about 4 μg of 17β-hydroxy-17α-[$^{131}$I]-iodoethynyl-18-methyl-4-estren-3-one with an approximately 70% radiochemical yield at a specific activity of about 259 MBq/4 μg (28.4 GBq/μmol). The chemical and radiochemical identity of the compound is confirmed by co-chromatography on TLC plates and analogous retention times in HPLC. For diagnostic and/or therapeutic usage, the solution is concentrated under vacuum, dissolved in ethanol/propylene glycol, and then subjected to sterile filtration.

The $^{123}$I, $^{125}$I, and $^{132}$I compounds are obtained analogously.

EXAMPLE 23

A solution is prepared from 5 μg (0.013 μmol) of 17α-bromoethynyl-17β-hydroxy-18-methyl-4-estren-3-one in 0.25 ml of acetone (p.a.), and heated under reflux for 3 hours under a protective gas in the presence of 370 MBq of sodium [$^{125}$I]-iodide (carrier-free) and 1 μg of copper sulfate.

After cooling to ice bath temperature, 0.25 ml of methanol, 0.1 ml of water, and 1 g of sodium iodide are added to the reaction mixture. In order to remove the ions, the solution is passed through a mixed bed ion exchanger, thus obtaining 2.3 μg of 17β-hydroxy-17α-[$^{125}$I]-iodoethynyl-18-methyl-4-estren-3-one having a specific activity corresponding to that of the Na [$^{125}$I]-iodide starting material. This specific activity thus ranges on the order of 80.29 GBq/μmol. The thus obtained 17β-hydroxy-17α-iodoethynyl-18-methyl-4-estren-3-one, labeled carrier-free with $^{125}$I, is separated from the starting compound by chromatography on silica gel on a low-pressure column in a system of hexane/acetone (acetone 10 ... 30%).

After concentration and taking up in ethanol/propylene glycol, a product is obtained which is suitable for diagnostic purposes.

EXAMPLE 24

50 μg (0.13 μmol) of 17β-hydroxy-17α-iodoethynyl-18-methyl-4-estren-3-one is dissolved in 50 μl of tetrahydrofuran, containing 1 μl of 0.5N hydrochloric acid, and added to 370 MBq of sodium [$^{82}$Br]-bromide, carrier-free. To this reaction solution is added 35 μg (0.125 μmol) of chloramine T (p-toluenesulfone[N-chloro-N-sodium]amide), dissolved in 5 μl of water.

After a reaction period of 2 hours, under repeated TLC control, the reaction solution is passed over a low-pressure column in a system of hexane/acetone (acetone 0 ... 30%), thus obtaining about 74 MBq of 17α-[$^{82}$Br]-bromoethynyl-17β-hydroxy-18-methyl-4-estren-3-one, labeled carrier-free with [$^{82}$Br]. The specific activity ranges at 80.5 TBq/mmol.

As described in connection with Example 22, the compound can be sterilized for diagnostic purposes.

As set forth in Examples 22 and 23, it is possible by analogous exchange with a radioactive bromine isotope, such as $^{77}$Br, $^{80m}$Br, $^{80}$Br, $^{82}$Br, to produce the bromineisotope-labeled compound in carrier free form as well as with a lower specific activity. The reaction is catalyzed by copper sulfate and is optionally carried out in hexamethylphosphoric triamide or other high-boiling polar solvents in order to obtain a higher velocity constant.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing an unlabeled or radioactively labeled 17α-bromoethynyl- or 17α-iodoethynyl-17β-hydroxy androstane or estrane of the partial formula

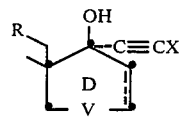

wherein is a single or double bond,

V is a carbon-carbon bond or a methylene group,

R is hydrogen or methyl, and

X is bromine or iodine, comprising reacting a corresponding 17α-ethynyl-17β-hydroxy androstane or estrane in an inert solvent with at least a stoichiometric amount of brominating agent or an iodinating agent in the presence of a catalytically effective amount of silver cations.

2. A process of claim 1 wherein the amount of silver is 0.001 to 1.0 molar equivalent.

3. A process of claim 1 wherein the silver is added in the form of the nitrate, perchlorate, acetate, trifluoroacetate, fluoride or sulfate.

4. A process of claim 1 wherein a brominating agent is used which is N-bromosuccinimide, N-bromoacetamide, N-bromophthalimide, N-bromo-p-toluenesulfamide, N-bromo-p-toluenesulfimide, N-bromocaprolactam, sodium hypobromide, or 1,3-dibromo-5,5-dimethylhydantoin.

5. A process of claim 1 wherein an iodinating agent is used which is N-iodosuccinimide.

6. A process of claim 1 wherein the solvent is a ketone, a cyclic ether, an aliphatic polyether, an aromatic hydrocarbon, an aliphatic alcohol, dimethylformamide, dimethylacetamide, hexamethylphosphoric triamide, N-methylpyrrolidone, or a mixture of water and a water miscible solvent.

7. A process of claim 1 wherein the starting estrane or androstane has at least a double bond in the 4-, 5-, 5(10)-, 6-, 8-, 9(11)-, 11-, or 15-position; an aromatic unsaturation in the 1,3,5(10)-positions; a 1-, 6- or 11- $C_{1-4}$-alkyl or $C_{2-4}$-alkenyl group; a 3-$C_{1-4}$-alkoxy group; or a combination thereof.

8. A process of claim 1 which is carried out at 0°–50° C., for 10 minutes to 20 hours.

9. A process of claim 1 wherein the brominating or iodinating agent is radioactively labeled whereby the resultant 17α-Br- or I-steroid is radioactively labeled.

10. A process of claim 1 wherein the product steroid is of the formula I or II

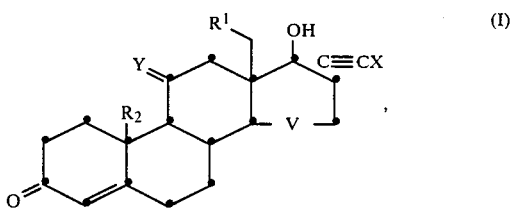

-continued

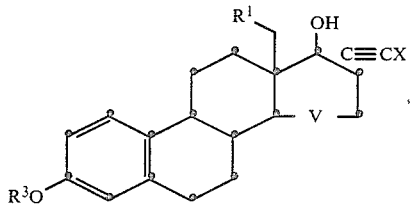

wherein is a single or double bond,

X is Br or Cl,

V is a C-C bond or a methylene group,

Y is two hydrogen atoms or a methylene group, $R^1$ and $R^2$ each independently is hydrogen or methyl, and $R^3$ is $C_{1-4}$-alkyl or, when X is bromine, also hydrogen.

11. A process for preparing a radioactively labeled 17α-bromoethynyl- or 17α-iodoethynyl-17β-hydroxy steroid, comprising heating the corresponding unlabeled 17α-bromo- or 17α-iodoethynyl compound with a solution of radioactively labeled bromide or iodide anions.

12. A process of claim 1 carried out in the presence of a catalytic amount of copper sulfate.

13. A process of claim 1 carried out in acetone under reflux.

14. A 17α-bromoethynyl- or 17α-iodoethynyl-17β-hydroxy steroid of Formulae I or II

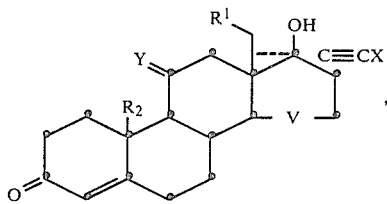

-continued

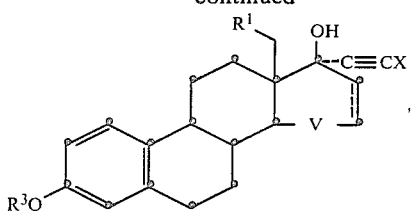

wherein is a single or double bond,

X is Br or I,

V is a C-C bond or a methylene group,

Y is a methylene group, $R^1$ and $R^2$ each independently is hydrogen or methyl, and $R^3$ is $C_{1-4}$-alkyl or, when X is bromine, also hydrogen.

15. A compound of claim 14 wherein V is a C-C bond.

16. A compound of claim 14 wherein X is a radioactive isotope of iodine or bromine.

17. A pharmaceutical composition comprising an effective amount of a compound of claim 14 and a pharmaceutically acceptable carrier.

18. A composition of claim 17 wherein the active compound has progestational activity and is of Formula I.

19. A composition of claim 17 wherein the active compound has estrogenic activity and is of Formula II.

20. A diagnostic pharmaceutical composition comprising an effective amount of a compound of claim 16 and a pharmaceutically acceptable carrier.

21. In a method of making a medical diagnosis comprising administering to a patient an effective amount of a radioactively labeled compound and then scanning the body of the patient with a radioactivity sensitive detector, the improvement wherein the radioactively labeled compound is one of claim 14.

22. A method of achieving a progestational effect in a patient in need of such treatment comprising administering to the patient an effective amount of a composition of claim 18.

23. A method of achieving an estrogenic effect in a patient in need of such treatment comprising administering to the patient an effective amount of a composition of claim 19.

24. A 17α-bromoethynyl-18-methyl-11-methylene-4-estren-17β-ol, a compound of claim 14.

25. A 17α-bromoethynyl-17β-hydroxy-18-methyl-4,15-estradien-3-one.

26. A process of claim 1, wherein V is a carbon-carbon bond.

* * * * *